United States Patent [19]

Swenson

[11] Patent Number: Plant 5,588

[45] Date of Patent: Dec. 3, 1985

[54] GRAPEVINE

[75] Inventor: Elmer Swenson, Osceola, Wis.

[73] Assignee: Swenson-Smith Vines, Inc., Excelsior, Minn.

[21] Appl. No.: 574,874

[22] Filed: Jan. 30, 1984

[51] Int. Cl.[4] ..... A01H 5/03

[52] U.S. Cl. ..... Plt./47

[58] Field of Search ..... Plt./47

*Primary Examiner*—Robert E. Bagwill

*Attorney, Agent, or Firm*—Merchant, Gould, Smith, Edell, Welter & Schmidt

[57] ABSTRACT

A grapevine which exhibits winter hardiness to −35° Fahrenheit in central or southern Wisconsin and Minnesota, produces a white wine of good quality, a grape with low-acidity, average sugar content and a flavor or aroma without the typical foxiness or labrusca of previous varieties.

3 Drawing Figures

ORIGIN AND REPRODUCTION

The present invention relates to a new and distinct variety of grapevine which has been produced by me as a result of an ongoing grape breeding program at my vineyard and nursery located in Polk County, near Osceola, in northern Wisconsin. The present variety is characterized by good winter hardiness and usefulness as a wine grape, having desirable aroma, flavor, acidity and sugar content, with no foxiness or labrusca flavor or aroma.

For some 40 years, I have been growing a large number of grapevines at my above-noted nursery and vineyard in northern Wisconsin with a breeding program directed to the production of grapevines having the desirable winter hardiness for northern states and also commercially useful as wine and/or table grapes.

By way of background, it is noted that there have been very few desirable commercial grape varieties for growing in the relatively harsh northern climate of Minnesota, Wisconsin, and similar northern states. Although this northern region has a summer thermal accumulation similar to that of the best grape growing areas of the world, the low winter temperatures have generally prevented development of vineyards in this region because of the lack of suitably hardy grape varieties.

The typical vineyard cultural practices in the noted northern regions generally involve early fall pruning, after which the vines are removed from trellises and laid upon the ground and covered for wintering. In the spring, the vines are uncovered and retrellised, all of which involves considerable labor costs, which are generally prohibitive and make it quite difficult for northern vineyards in such climates to operate profitably. Accordingly, for grapevines to be of high commercial value to vineyards in such northern regions, such as Minnesota and Wisconsin, it has become nearly essential that the varieties be hardy enough to remain on the trellises throughout the winter months without removal and winter covering. The present variety has this desirable characteristic for the southern, or even central, portions of the northern tier of states.

This new variety of grapevine was selected by me for its combination of good winter hardiness and usefulness as a wine grape, producing a white wine similar to the Seyval which is one of its parents.

The present variety is a result of my above-noted breeding program, in which my varietal selections are designated by number with the prefix ES. This variety is a select seedling resulting from my cross of ES114 X Seyval. I have identified the present variety as EX294 and selected the name "LaCrosse" therefor.

I have reproduced the present variety by means of vine cuttings and have carefully observed the variety for several years. The continual observation and testing of the present variety has convinced me that it is a new and improved cultivar of grapevine, as indicated by the following unique combination of outstanding qualities which distinguish this variety from all other varieties of grapevine known to me.

SUMMARY OF CHARACTERISTICS

The unique combination of characteristics of the present variety ES294, named "LaCrosse", are as follows:

1. Winter Hardiness. The present variety has excellent winter hardiness for zones such as the southern portion of Minnesota and Wisconsin, or even to the central portions of such states, whereby the vines may remain on the trellises throughout the winter without covering. More specifically, this variety has survived on trellises with a winter temperature of −35° Fahrenheit with no apparent injury to its vines or buds thereon and with no winter covering. Such survival has been at my vineyard located near Osceola, Wisconsin, and at a secondary test site located near Redwood Falls, Minn. My observations indicate this variety to be several degrees more winter hardy that the Seyval variety which is its pollen parent.

2. Low Acidity. The present variety has also produced grapes of relatively low acidity for a cold climate grape, a desirable attribute for wine grapes. In years of relatively poor growing conditions, this vine's acidity has averaged 1.2% and in years of good growing conditions its acidity has averaged 0.85%.

3. Sugar Content. The sugar content of this cultivar has been tested at a northern test site located at Mr. David MacGregor's vineyard near the western portion of Wright County, South Haven, Minn., and the average sugar content was 18.2° Brix. The sugar content was also tested at a more southern test site, the vineyard of Mr. Robin Partch near Redwood Falls, Minn., and the average sugar content was 18.2° Brix.

4. Flavor and Color. The typical foxiness or labrusca flavor and aroma which is an objectionable characteristic generally for wine grapes, yet is typical of previous varieties having good winter hardiness, is not apparent in this variety. The variety produces a white wine that compares favorably with many German style white wines.

ASEXUAL REPRODUCTION

The present variety has been asexually reproduced by me by means of vine cuttings at my nursery and vineyard in Polk County, Wisc. Such asexual reproduction confirms that the characteristics and qualities stated herein for this variety are true to form and consistent through succeeding propagation.

DETAILED DESCRIPTION

The accompanying drawings comprise photographs showing characteristics of this new variety. The photographs were taken of specimens of the variety growing under typical vineyard conditions. The color photographs depict color features as true as reasonably possible.

Figure 2:
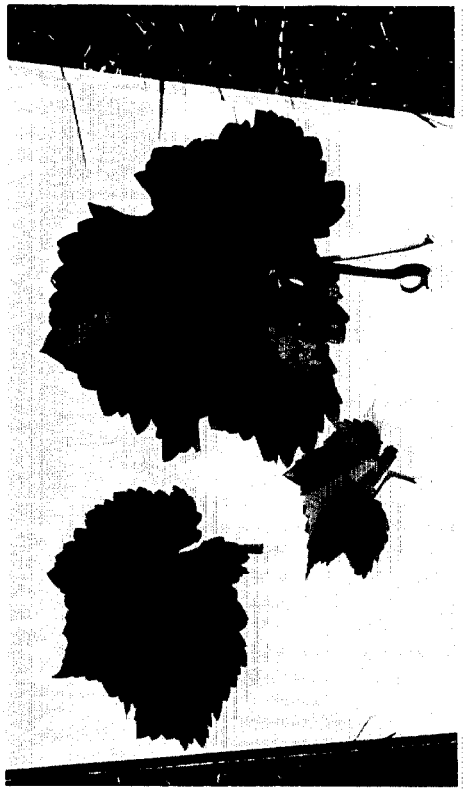
FIG. 2 is a color photograph showing the mature summer leaf form for typical leaves of the variety.
Figure 3:
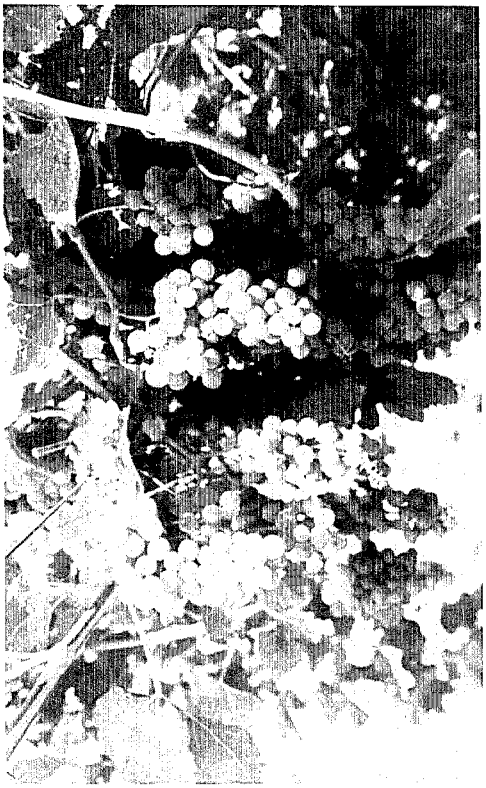
FIG. 3 is a color photograph showing typical fruit clusters of the present variety.
Figure 1:
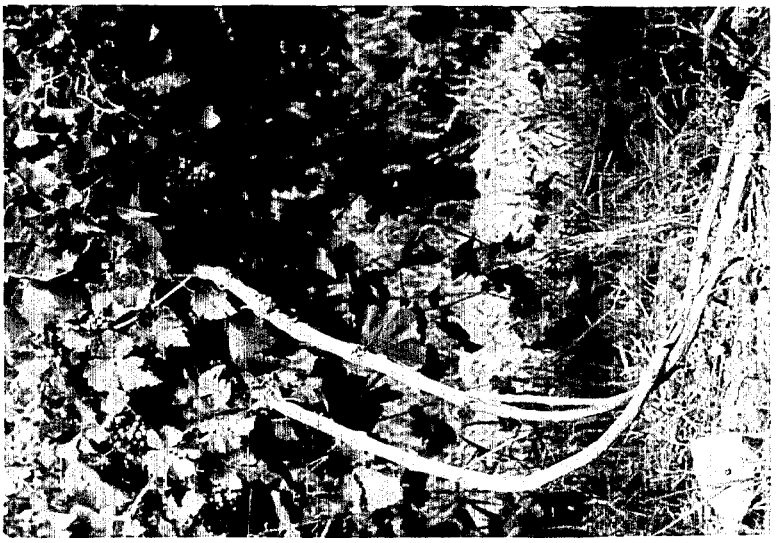
FIG. 1 is a color photograph showing the form and growth of a mature vine of the present variety.

The following is a detailed description or specification of the pomological characteristics of this new variety, with color terminology or references in accordance with The Royal Horticulture Society Colour Chart. Where dimensions, sizes, colors, and other characteristics are given, it is to be understood that the same are approximations of averages as they appear under conditions prevailing at the noted secondary test sites near Redwood Falls and South Haven, Minn., as well as my vineyard near Osceola, Wisc.

Vine:

*Growth habit.*—Somewhat upright but not as pronounced as its pollen parent, Seyval. Tends to form a somewhat open canopy. Medium vigorous to vigorous.

*Trunk.*—Thick and sheds bark in long strips but trunk needs support. Inner bark color between Greyed Orange Color Group 174C and Greyed Orange Color Group 174D.

*Canes.*—Average length is 2.1 meters. Spacing between nodes averages 10.4 centimeters. Tendrils are intermittent (skip every third node).

Foliage:

*Leaves.*—Top sinuses often deep, narrow and tend to cause lobes to overlap at a sinus when the leaf is pressed. Petiole sinus ogive shape with petiole joining at the apex. Mature leaf color (top) close to Green Group 137A; leaf underside closest to Yellow Green Group 146B; petiole is Yellow Green Group 144D. Average mature leaf is approximately 11 centimeters wide by 13 centimeters long.

Grapes:

*Maturity.*—Early mid-season. Early September to mid-September at Redwood Falls, Minn. Often ripens one week earlier than Seyval grape.

*Size of berry.*—Natural 1.3 centimeter average.

*Shape of berry.*—Spherical.

*Ripening.*—Ripens evenly. Fruit holds well on the vine with no shattering.

*Color of berry.*—Between Yellow Green 144A and Yellow Green 144B.

*Cluster.*—Typically not "V" shouldered and typical shape would be more cylindrical than cone-shaped. Medium clusters which measure: 2 centimeters stem; 6 centimeter cluster width; 11 centimeter length (stem length omitted). Average cluster weight is approximately 4 ounces. Approximately 60–65 berries per cluster. 2 to 3 clusters per shoot.

*Seeds.*—2.4 average seeds per berry. Seed color: light brown. Seed shape: short and plump like a Riparia, but larger.

*Pulp.*—Tender and juicy, not stringy. Pulp color close to Yellow Green 150D.

*Juice color.*—Free run juice is close to Green White 157B.

*Sugar and acid.*—19.0° Brix and 0.85 acid (Sept. 17, 1983).

*Clusters per shoot.*—Usually three.

*Other characteristics.*—Perfect flowers, self-pollinating. Appears resistant to mildew on the fruit and 2-4-d. Susceptible to phylloxera as leaf galls only. Moderately susceptible to downy mildew on the leaves.

I claim:

1. A new and distinct variety of grapevine, substantially as shown and described herein, characterized particularly as to novelty by the unique combination of winter hardiness down to −35° Fahrenheit in central or southern Wisconsin and Minnesota, producing white grapes which made a good quality of wine comparable to a German style white wine, and grapes with relatively low acidity, average sugar content and a flavor or aroma absent the typical foxiness or labrusca of earlier varieties.

* * * * *